United States Patent
Mesaros et al.

(10) Patent No.: US 6,821,250 B2
(45) Date of Patent: Nov. 23, 2004

(54) DIAGNOSTIC ULTRASOUND SYSTEM CART WITH MOVABLE PROBE HOLDERS

(75) Inventors: Robert Mesaros, Bothell, WA (US); Yas Matsui, Redmond, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/155,506

(22) Filed: May 23, 2002

(65) Prior Publication Data

US 2003/0236463 A1 Dec. 25, 2003

(51) Int. Cl.⁷ .................................................. A61B 8/00
(52) U.S. Cl. ............................................................ 600/437
(58) Field of Search ................................ 600/437–471; 73/625, 626; 367/7, 11, 130

(56) References Cited

U.S. PATENT DOCUMENTS

| | | | |
|---|---|---|---|
| 4,625,731 A | 12/1986 | Quedens et al. | |
| 4,870,954 A | * 10/1989 | Satoh | 601/4 |
| 5,129,397 A | 7/1992 | Jingu et al. | |
| 5,205,175 A | 4/1993 | Garza et al. | |
| 5,615,678 A | * 4/1997 | Kirkham et al. | 600/459 |
| 5,615,682 A | * 4/1997 | Stratz, Sr. | 600/459 |
| 5,924,988 A | * 7/1999 | Burris et al. | 600/437 |
| 5,941,824 A | 8/1999 | Hwang | |

* cited by examiner

*Primary Examiner*—Ali Imam
(74) *Attorney, Agent, or Firm*—W. Brinton Yorks, Jr.

(57) ABSTRACT

An ultrasound system has a plurality of locations around the control panel at which a probe holder may be located. The probe holder may be mounted by the user on the left or right side of the control panel to accommodate left-handed or right-handed users. The illustrated embodiments show different mechanisms by which a probe holder may be movably mounted to the ultrasound system. In one embodiment a plurality of probe holders swing or slide out for use, and stow inside the system when not in use.

15 Claims, 12 Drawing Sheets

Figure 1:
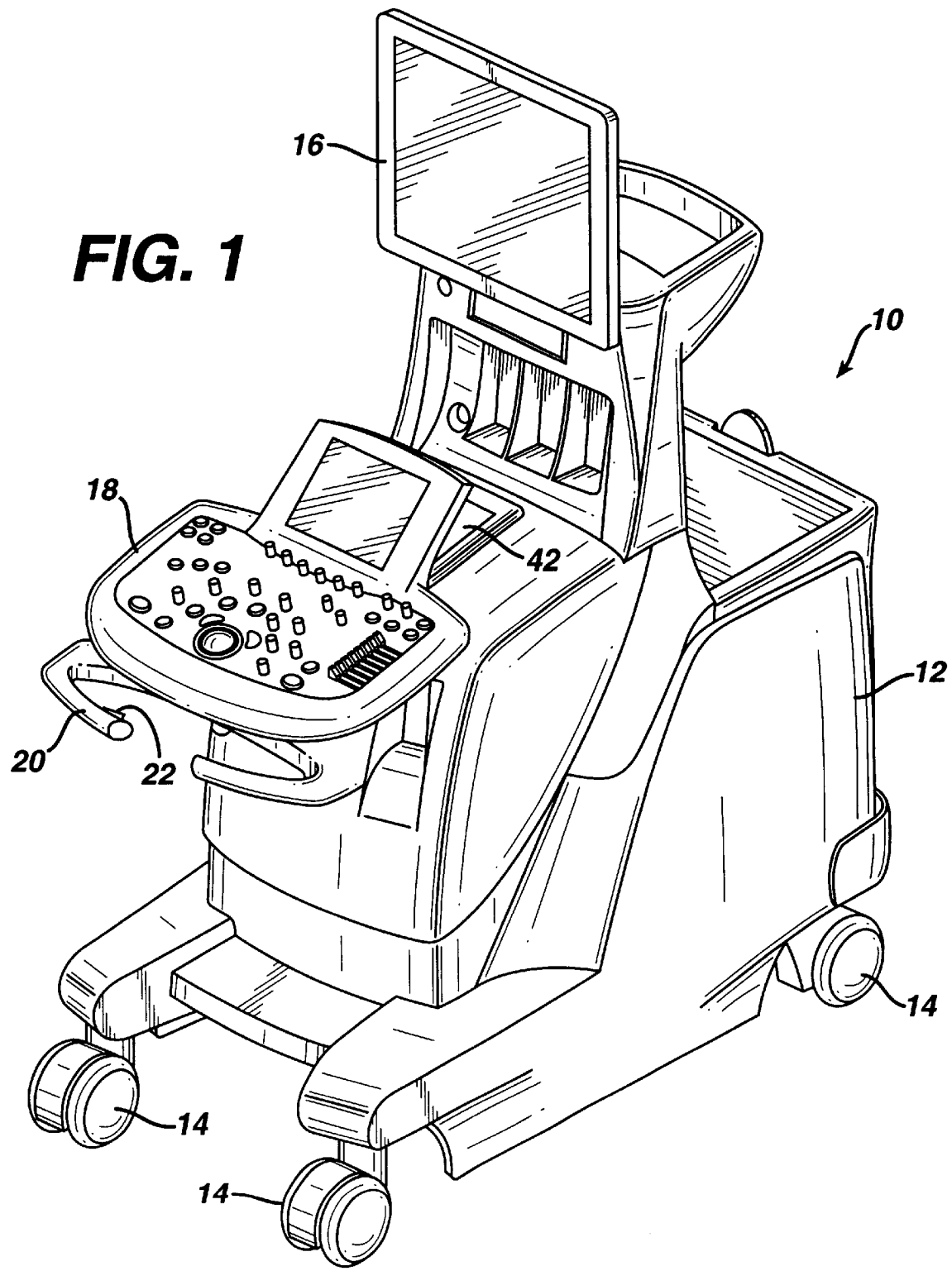

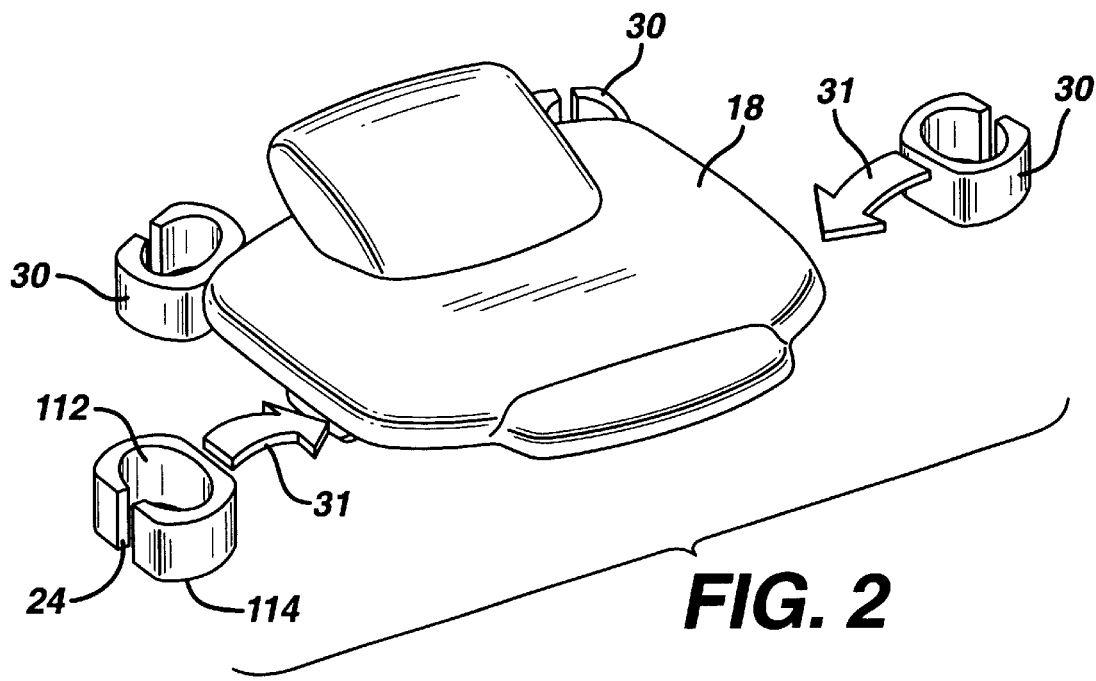
FIG. 2
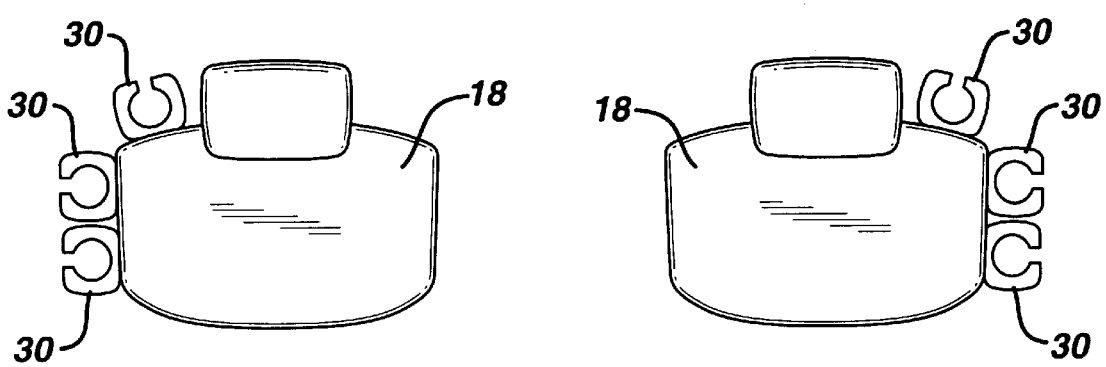
FIG. 3a          FIG. 3b

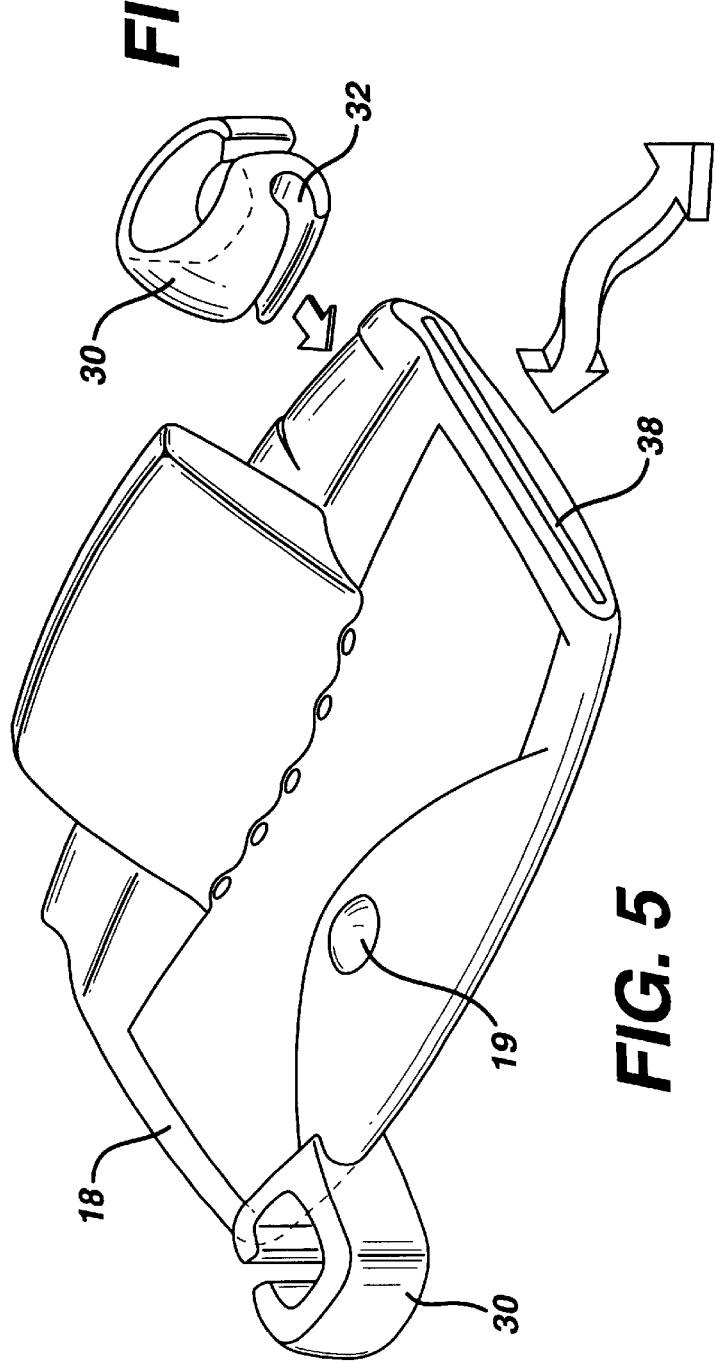
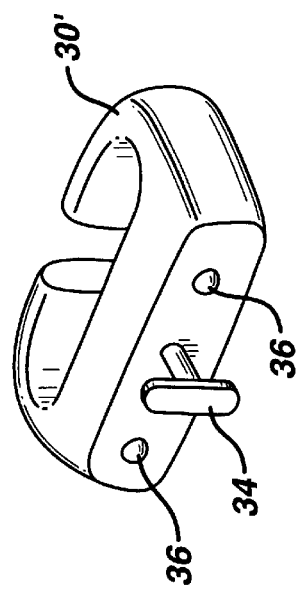
FIG. 5b
FIG. 5a
FIG. 5

DIAGNOSTIC ULTRASOUND SYSTEM CART WITH MOVABLE PROBE HOLDERS

This invention relates to ultrasonic diagnostic imaging systems and, in particular, to ultrasound systems with probe holders that can be moved to a convenient position on the system.

Cart-borne ultrasound systems are designed to be operated with at least one, and generally several, different probes connected to the system at the same time. The multiple connections allow the operator to change probes by simply selecting a different one of the connected probes. When not in use, the connected probe is placed in a probe holder on the cart. The probe holders are often formed on one side of the control panel, or may comprise a tray in front of or behind the control panel. However, the probe holders may not be in a place which is convenient for all users. Left-handed users may find it inconvenient to have the probe holders on the other side of the control panel. Other users may find that the probe holders are in the back of the control panel when they would prefer to have them in front. At times the probe holder will be too close to the probe connector, causing the probe cable to drag on the floor where it can pose a hazard or be damaged. Accordingly it is desirable for the user to be able to configure the probe holder locations to be in the most convenient location for his own personal use of the ultrasound system.

In accordance with the principles of the present invention, an ultrasound system is provided with movable probe holders. The illustrated embodiments show various ways in which a probe holder can be removably attached to an ultrasound system, and various selectable locations for probe holders around the system control panel. Among the mounting means disclosed are clips, clamps, screws, plugs and guide pins for connecting a movable probe holder to the ultrasound system. In one embodiment the probe holders can be pulled out from beneath the control panel and pushed back in when not needed. The movable probe holders may also be configured to hold a gel bottle if desired.

Figure 4:
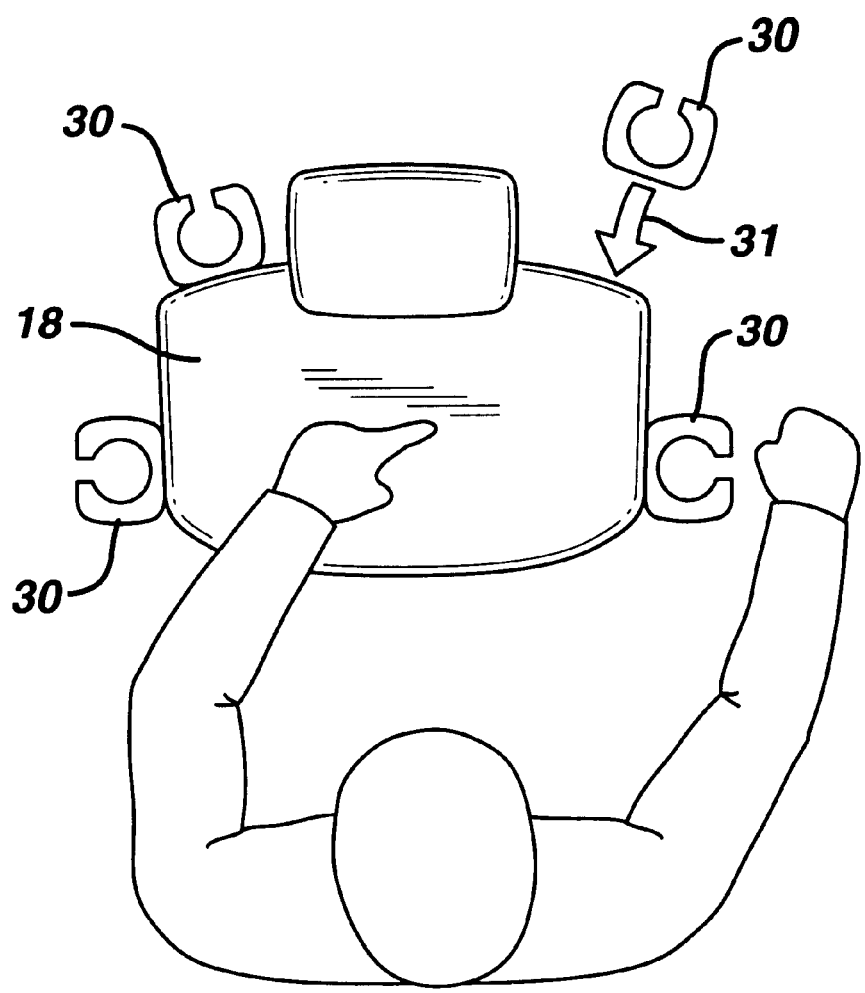
Figure 6A:
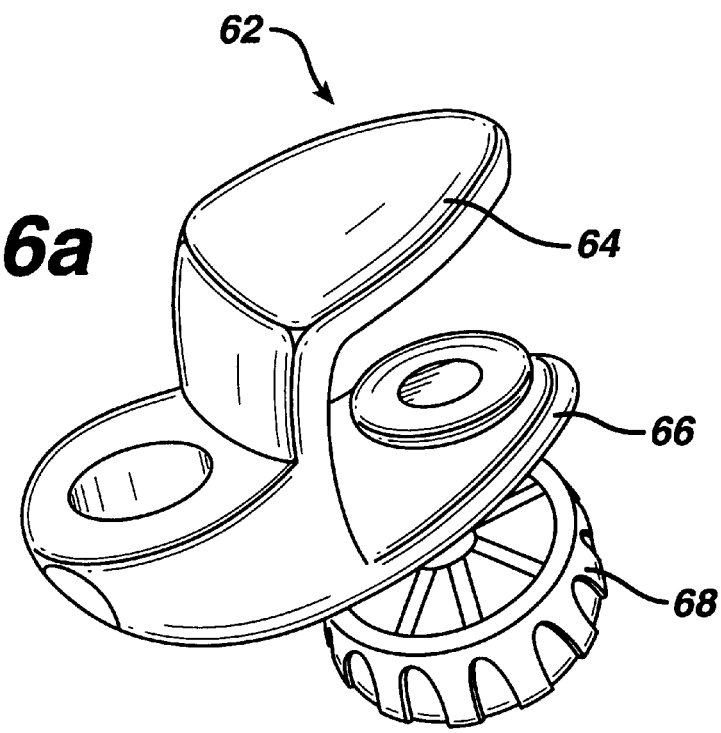
Figure 6B:
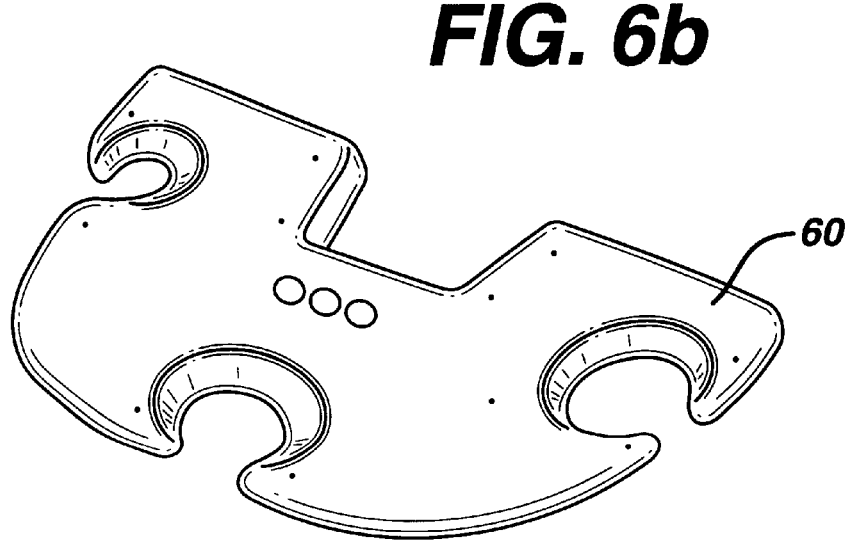
Figure 7:
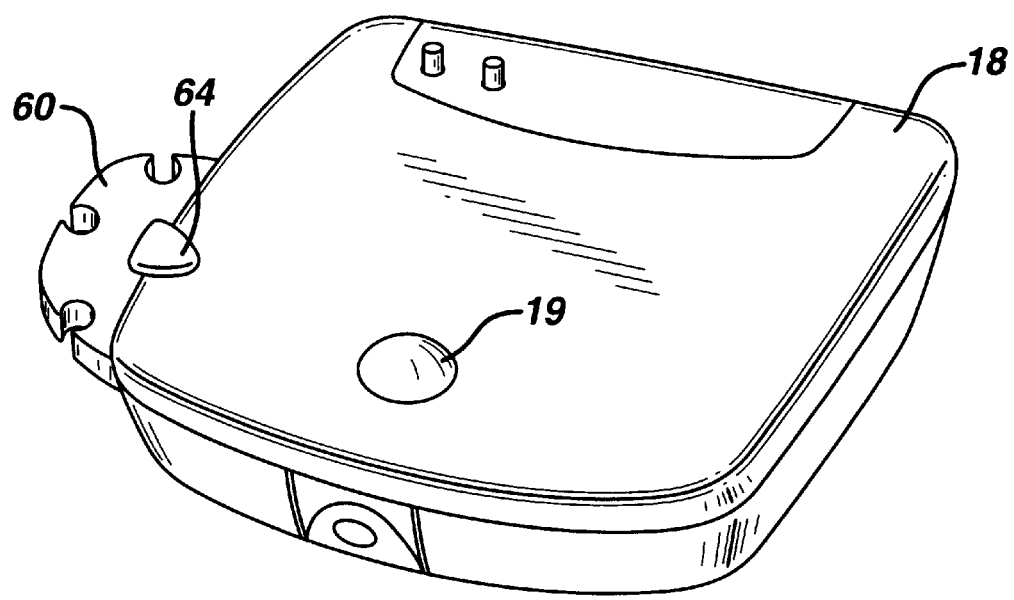
Figure 8:
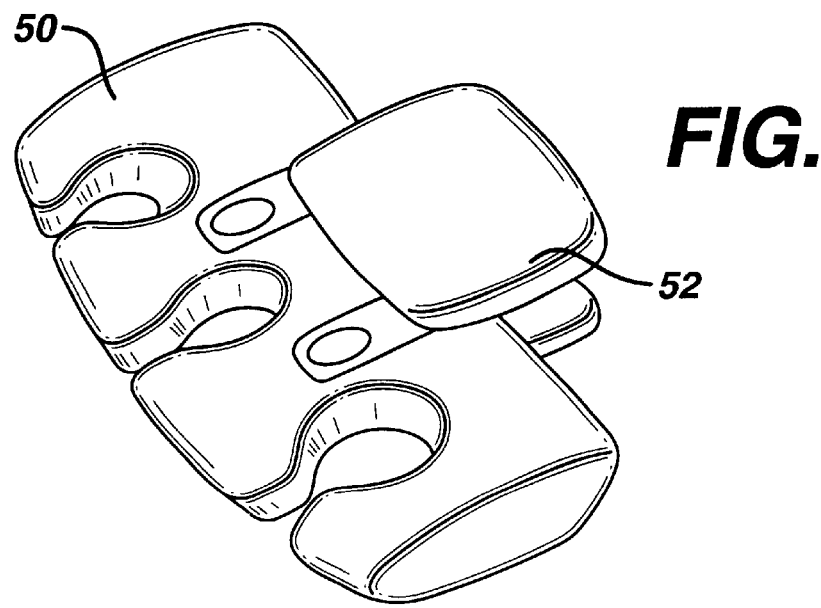
Figure 9A:
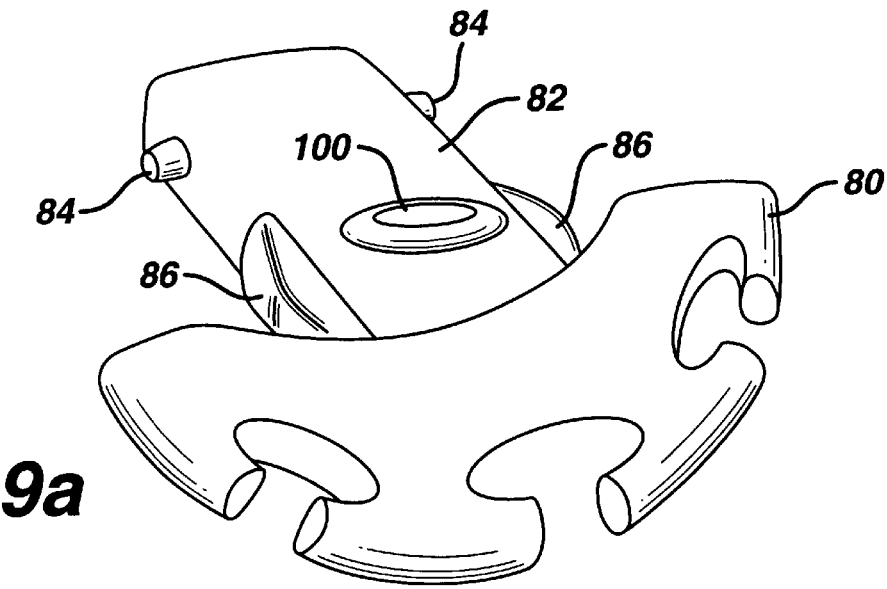
Figure 9B:
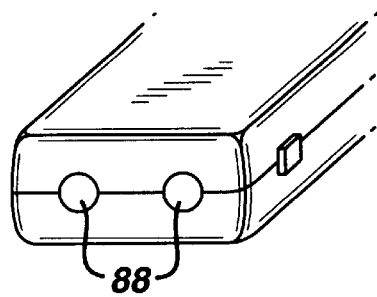
Figure 9C:
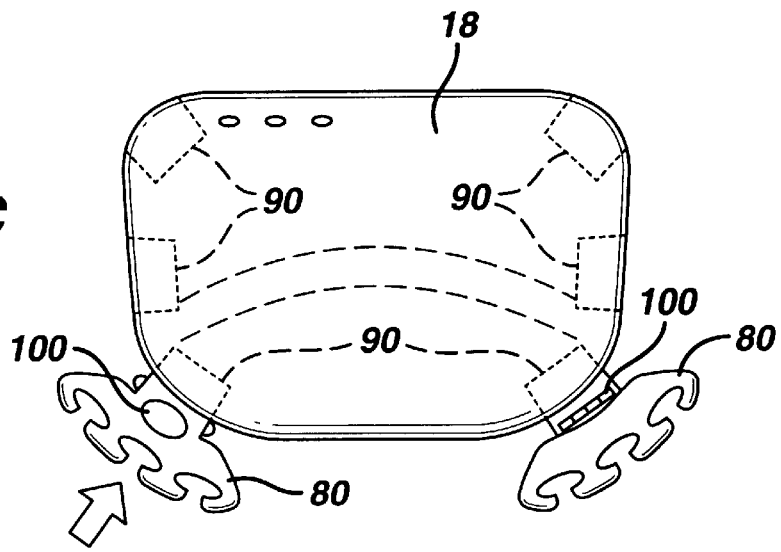
Figure 10:
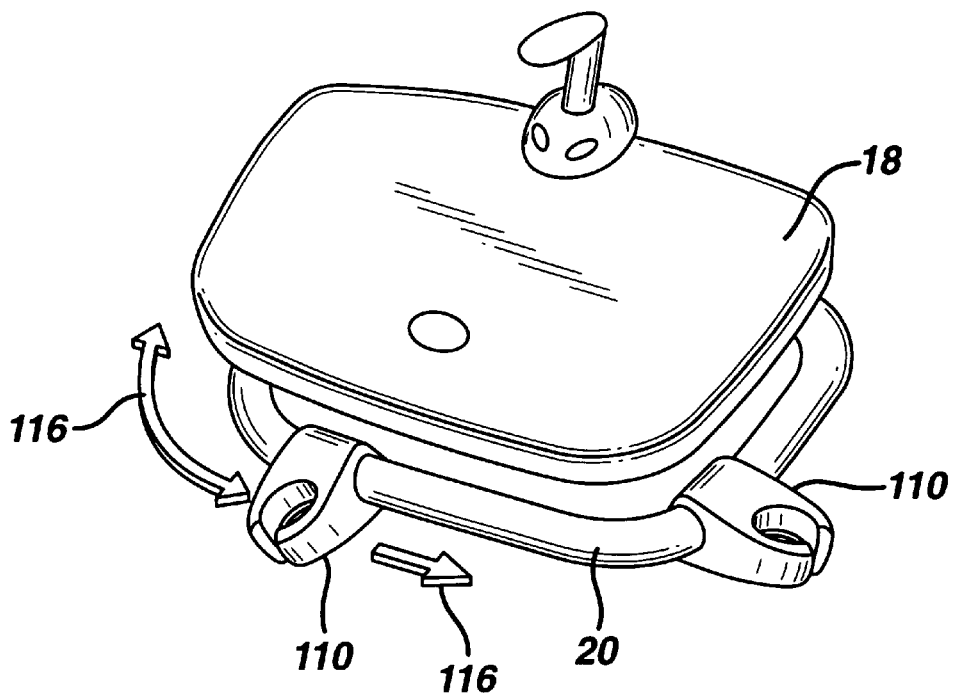
Figure 10A:
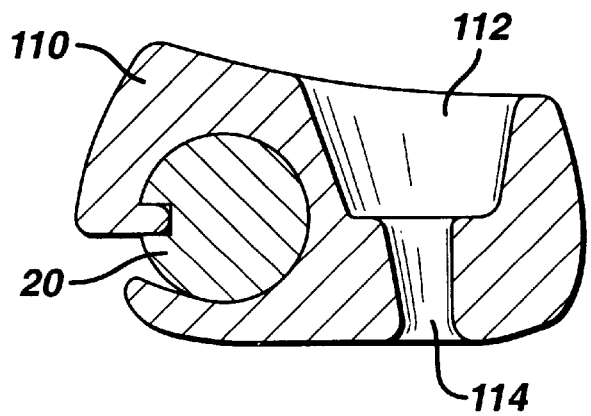
Figure 11A:
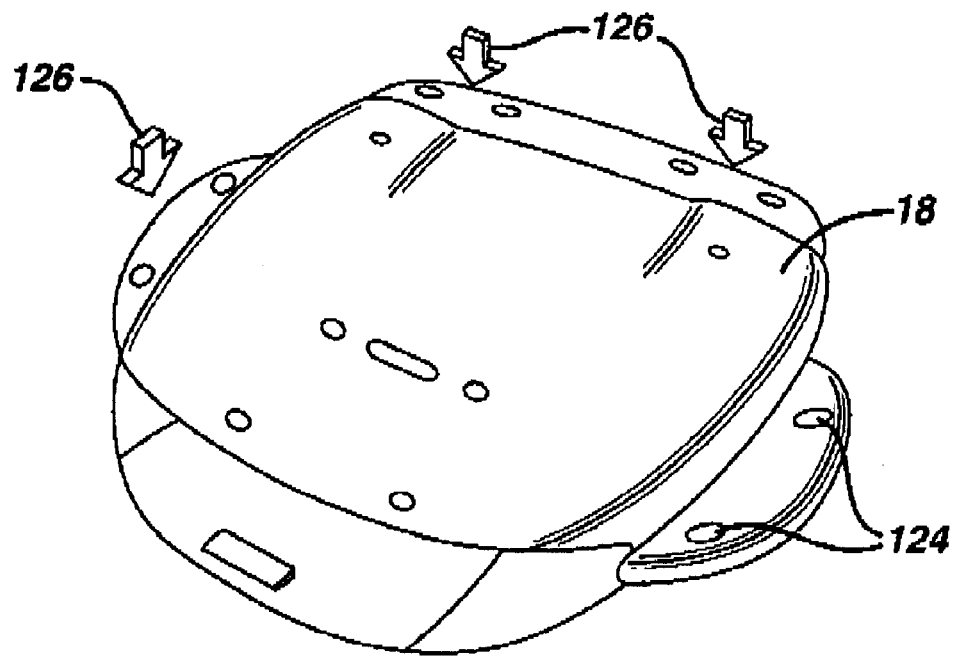
Figure 11B:
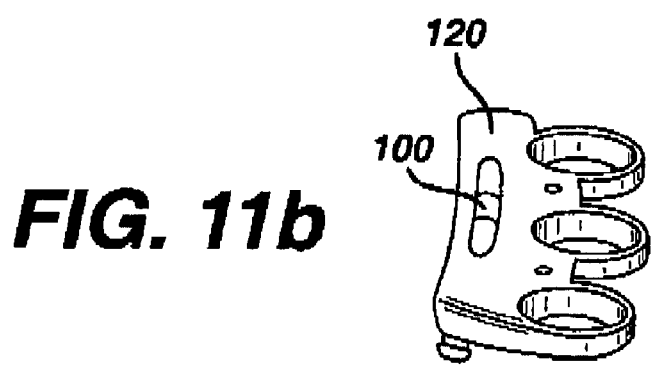
Figure 11C:
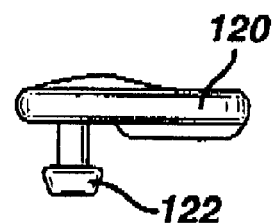
Figure 12:
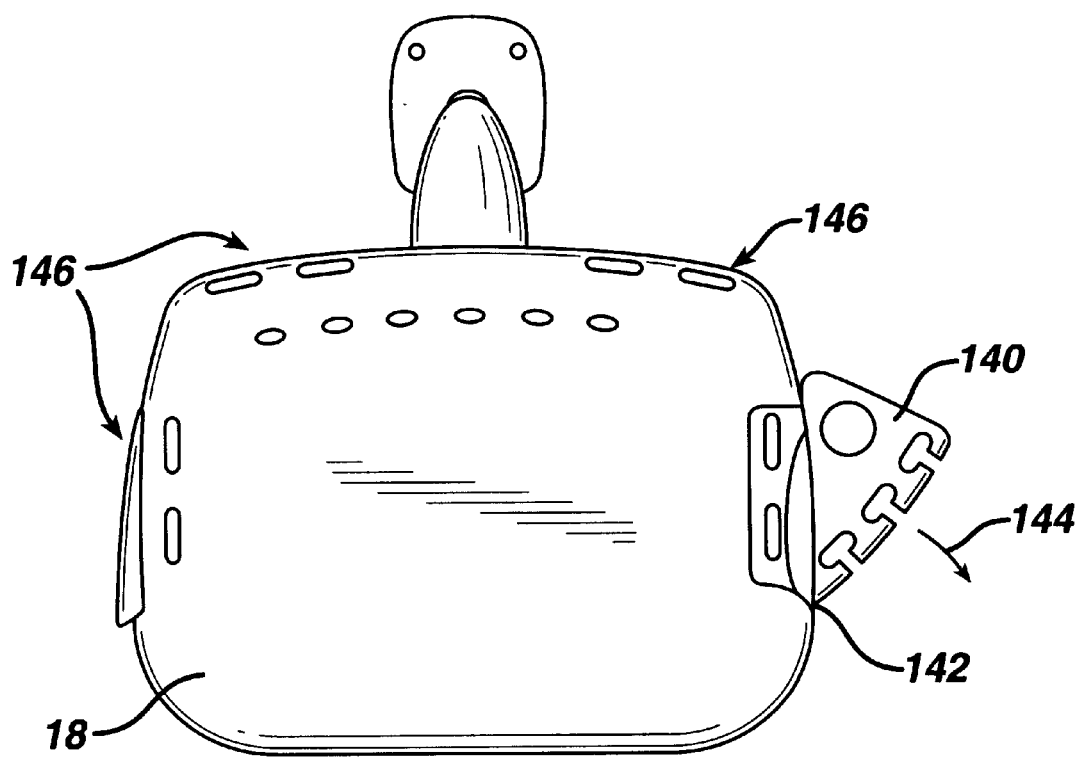
Figure 13A:
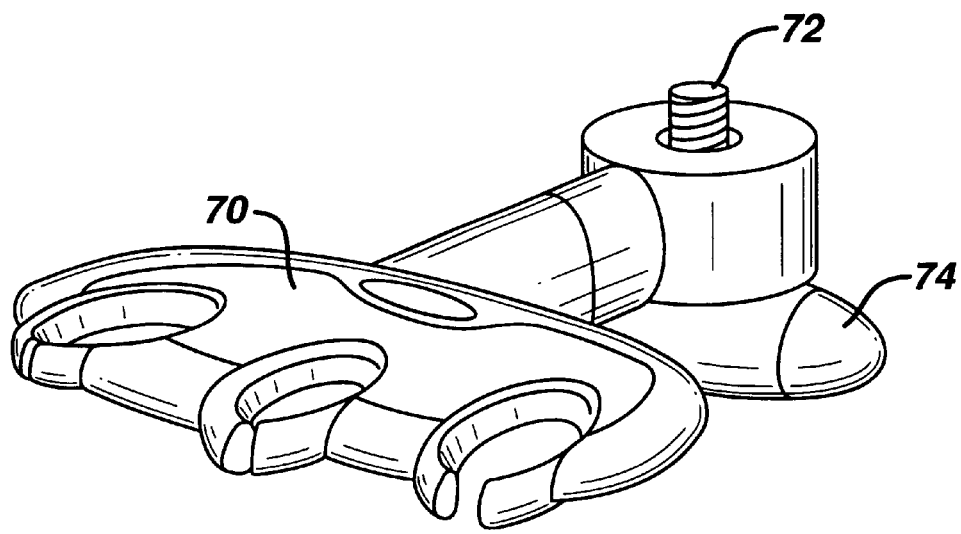
Figure 13B:
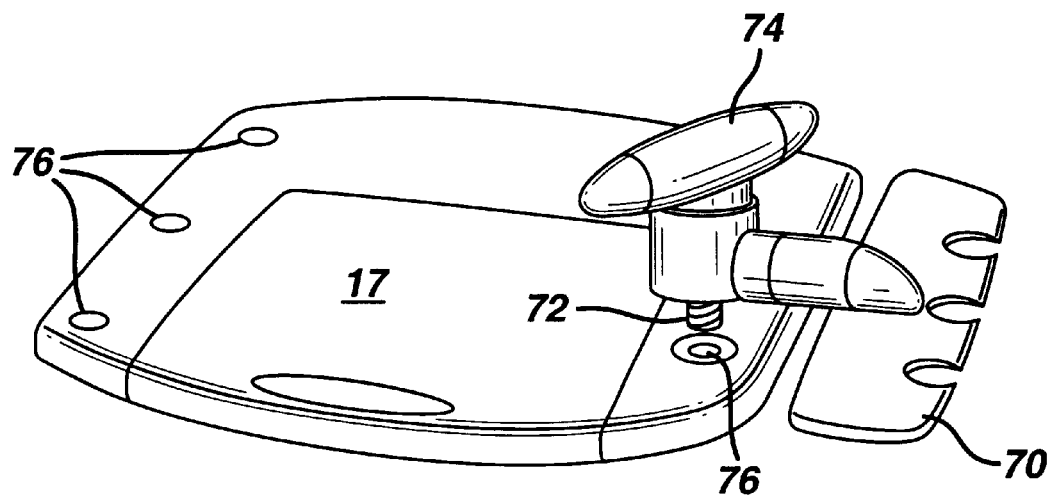

In the drawings:

FIG. 1 illustrates a cart-borne ultrasound system in perspective;

FIGS. 2, 3, and 4 illustrate a plurality of locations around an ultrasound system control panel at which probe holders in accordance with a first embodiment of the present invention may be located;

FIGS. 5, 5a, 5b and 5c illustrate probe holders which snap onto and slide along the side of an ultrasound system control panel in accordance with further embodiments of the present invention;

FIGS. 6a, 6b, and 7 illustrate a two-piece, clamping probe holder in accordance with another embodiment of the present invention;

FIG. 8 illustrates a one-piece clamping probe holder in accordance with a further embodiment of the present invention;

FIGS. 9a, 9b, and 9c illustrate probe holders which may be removably plugged into different locations around an ultrasound system in accordance with another embodiment of the present invention;

FIGS. 10 and 10a illustrate probe holders which slide around the front and sides of an ultrasound system in accordance with another embodiment of the present invention;

FIGS. 11a, 11b, and 11c illustrate a probe holder with post mounts in accordance with another embodiment of the present invention;

FIG. 12 illustrates a further embodiment of the present invention in which probe holders slide out from beneath the control panel of an ultrasound system; and FIGS. 13a and 13b illustrates a probe holder which is removably screwed into different locations around an ultrasound system in accordance with another embodiment of the present invention.

Referring first to FIG. 1, a cart-borne ultrasound system 10 is shown in perspective. The cart includes an electronics bay 12 inside of which are located printed circuit boards for electronically processing received ultrasound signals. The ultrasound signals are processed to produce an image which is displayed on a display 16. The cart is mounted on wheels or casters 14 so that it can be rolled to a lab or a patient's bedside. In the front of the cart is a control panel 18, which contains a number of knobs, buttons, slide switches, and a trackball by which a user controls the operation of the ultrasound system. The control panel is mounted above a handle 20 which extends from the front of the ultrasound system. The handle 20 can be used to pull the cart to move it from one location to another. On the inside of the handle 20 is a lift release button 22 which unlocks a lift mechanism 42 for the control panel, enabling the control panel to be raised or lowered to an elevation which is comfortable for the user. The lift mechanism is more fully described in concurrently filed U.S. patent application Ser. No. 10/154,733 the subject matter of which is incorporated herein by reference.

FIG. 2 illustrates the control panel 18 of an ultrasound system around which one or more probe holders 30 may be positioned. The probe holders 30 are removably mounted around the control panel as indicated by the arrows 31. In this embodiment the probe holders 30 have a slot 24 in the side through which one may pass the cord of a probe. Each holder has a large diameter opening 112 at the top, an interior base or taper (not shown in this drawing), and a smaller diameter hole 114 at the bottom (better seen in FIG. 10a) through which the probe cable extends when the probe is placed in the holder. Preferably the large diameter opening is sufficiently large to accommodate the diameter of a gel bottle, enabling the probe holder to serve as either a gel bottle holder or a probe holder.

FIGS. 3a and 3b illustrate the probe holders 30 clustered on one side of the control panel or the other, as may be preferred by left-handed users or right-handed users. FIG. 4 illustrates a user at a control panel 18 which has probe holders located on both sides and at the left rear corner of the control panel 18. A fourth probe holder 31 is shown positioned for mounting at the right rear corner of the control panel as indicated by the arrow.

Figure 5C:
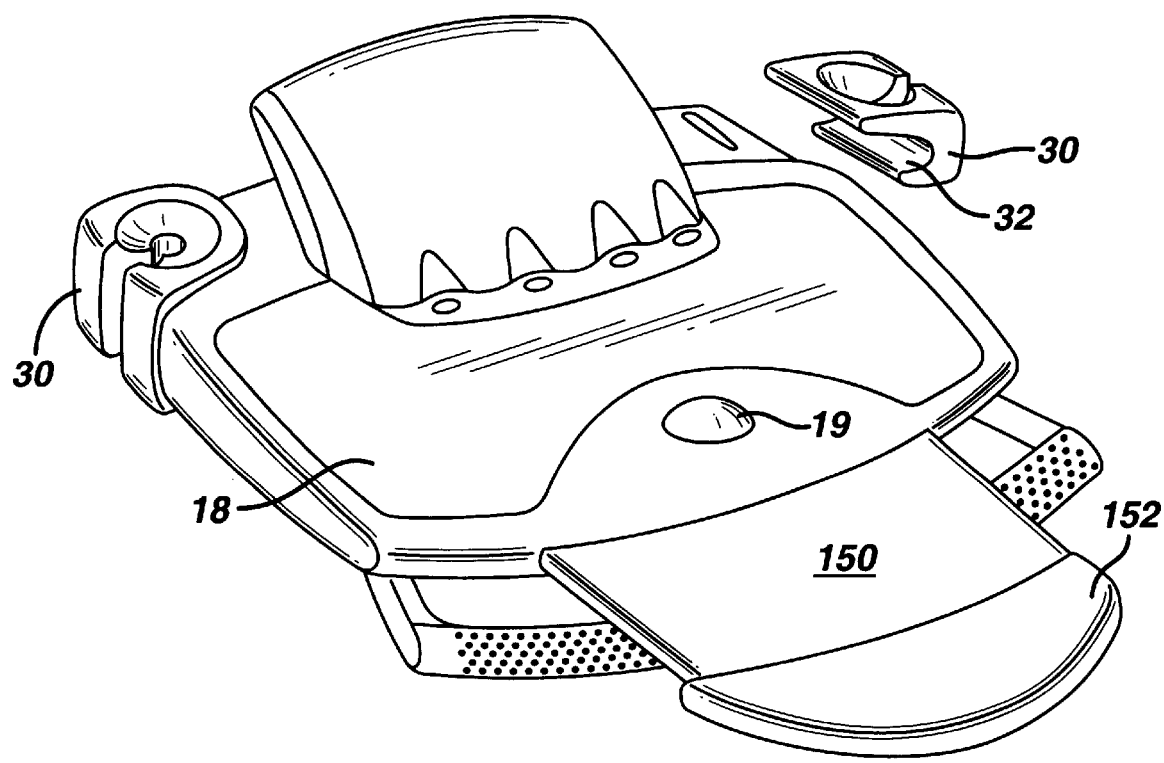

FIG. 5 illustrates a control panel 18 which utilizes two different kinds of probe holder attachment. Probe 30 in FIG. 5b has an integral groove 32 which clips onto the edge of the control panel, as indicated by the arrow between FIGS. 5 and 5b. FIG. 5 shows one such probe holder clipped onto the left front edge of the control panel 18. The control panel also has a T-shaped slot 38 on each side. This enables probe holder 30', shown in FIG. 5a, to be mounted on either side of the control panel. The probe holder 30' is turned 90° to insert a T-shaped pin 34 into slot 38, as indicated by the arrow between FIGS. 5 and 5a. The probe holder is turned back to its normal upright position and two spring-loaded pins 36 snap into the slot 38 to guide the probe holder as it adjustably slides along the side of the control panel 18. FIG. 5c illustrates a variation of this embodiment in which the probe holders 30 clip onto the sides of the control panel. FIGS. 5 and 5c also illustrate the usual location of a trackball control 19 in the front portion of the control panel. FIG. 5c illustrates a keyboard 150 with an integral wrist support pad 152 extending from the front of the control panel, as more fully described in concurrently filed U.S. patent application Ser. No. 10/155,504.

FIGS. 6a and 6b illustrate a probe holder 60 is attached to the ultrasound system by a clamping device 62. These drawings show the probe holder as a two-piece unit, although the holder may also be fabricated as a unitary structure. To attach the probe holder the upper mount plate 64 is placed on one side of the mounting surface and the knob 68 on the lower mount plate 66 is turned to tighten the clamp onto the system. FIG. 7 illustrates the probe holder 60 clamped on the left side of a control panel 18. Instead of a threaded clamp which is screwed on, the clamping device may be a spring-loaded or cam-actuated clamp 52 as shown on probe holder 50 in FIG. 8.

FIGS. 9a–9c illustrate a probe holder 80 with an insertion section 82 that is inserted in one of a series of engaging openings 90 around the periphery of a control panel 18. When the user squeezes the pushbuttons 86 on either side of the probe holder, pins 84 are retracted into the body of the insertion section 82, permitting the insertion section to be inserted into one of the openings 90. The pushbuttons are then released and the pins 84 spring out to lock the probe holder into the opening. The user removes the probe holder by depressing the pushbuttons to retract the pins and withdraw the probe holder from the opening. At the distal end of the insertion section are two electrical contacts 88, shown in FIG. 9b, which mate with two electrical leads inside the opening. These contacts provide electricity to power a small light 100 on top of the probe holders, which illuminate the probe holder 80 in a darkened examination room.

FIGS. 10 and 10a illustrate another embodiment of the present invention in which a bar or handle 20 extends around the front and sides of a control panel 18. One or more probe holders 110 may be mounted on the bar 20 as shown in the cross-sectional view of FIG. 10a. The probe holders can slide along the bar to be positioned as desired by the user, as indicated by the arrows 116. Preferably the probe holders 110 are made of a rubberlike or other deformable material so they can slide around the curves of the bar and be snapped or hooked onto and removed from the bar 20.

FIGS. 11a, 11b, and 11c illustrate another embodiment of the present invention in which the probe holder 120 has posts 122 which engage holes 124 around the periphery of the control panel, as indicated by arrows 126. The holes 124 may contain electrical contacts mating with conductors integrated into or comprising the posts 122, thereby providing a source of power to illuminate the light 100 on the probe holder 120.

FIG. 12 illustrates a further embodiment of the present invention in which a plurality of probe holders 140 are retractably located around the control panel 18. The probe holders 140 are normally stowed under the control panel, giving smooth, clean lines to the control panel. When a probe holder is needed, it is pivoted out from under the control panel 18 as indicated by arrow 144 and pivot point 142. Arrows 146 illustrate the positions of other stowed probe holders. Instead of pivoting out and back from the control panel, the probe holders can be mounted to slide out and then back under the control panel in the manner of small drawers. In either case, the probe holder would preferably have one detent position when fully stowed, and at least a second detent position when fully extended from its recess under the control panel.

FIGS. 13a and 13b illustrate another embodiment of the present invention in which a probe holder 70 is removably screwed into the control panel. FIG. 13b is a view of the underside 17 of a control panel which is seen to have a plurality of threaded holes 76. The threads 72 of the probe holder 70 engage one of these threaded holes, and the knob 74 is turned to screw the probe holder into place as illustrated in FIG. 13b.

What is claimed is:

1. A cart-borne ultrasound system having a control panel from which the system may be operated, and a hand-held probe connected to the system which transmits or receives ultrasound energy from a patient, comprising:

a probe holder which can be movably connected by a system operator independently of the probe connection at two or more locations on the system, wherein the control panel further includes two or more locations at which the probe holder can be movably connected.

2. The cart-borne ultrasound system of claim 1, wherein the probe holder includes a snap fit for attaching to the control panel.

3. A cart-borne ultrasound system having a control panel from which the system may be operated, and a hand-held probe connected to the system which transmits or receives ultrasound energy from a patient, comprising:

a probe holder which can be movably connected by a system operator independently of the probe connection at two or more locations on the system, wherein the probe holder includes a clamping device for clamping the probe holder at one of a plurality of locations around the control panel.

4. The cart-borne ultrasound system of claim 3, wherein the clamping device is spring-loaded.

5. The cart-borne ultrasound system of claim 3, wherein the clamping device is cam-actuated.

6. The cart-borne ultrasound system of claim 3, wherein the clamping device is threaded.

7. A cart-borne ultrasound system having a control panel from which the system may be operated, and a hand-held probe connected to the system which transmits or receives ultrasound energy from a patient, comprising:

a probe holder which can be movably connected by a system operator independently of the probe connection at two or more locations on the system, wherein the probe holder includes an insertion section which may be inserted into one of a plurality of recesses around the control panel.

8. The cart-borne ultrasound system of claim 7, wherein probe holder further includes an electrical light, and wherein the insertion section includes electrical contacts for powering the electrical light.

9. A cart-borne ultrasound system having a control panel from which the system may be operated, and a hand-held probe connected to the system which transmits or receives ultrasound energy from a patient, comprising:

a probe holder which can be movably connected by a system operator independently of the probe connection at two or more locations on the system, further comprising a bar mounted adjacent to the control panel, wherein the probe holder can be adjustably moved along the bar.

10. The cart-borne ultrasound system of claim 9, wherein the bar extends around the front and sides of the control panel.

11. A cart-borne ultrasound system having a control panel from which the system may be operated, and a hand-held probe connected to the system which transmits or receives ultrasound energy from a patient, comprising:

a probe holder which can be movably connected by a system operator at two or more locations on the system, wherein the probe holder further comprises one or more posts for mounting the holder, and wherein the ultrasound system further includes a plurality of engagement holes for engaging one or more of the posts of a probe holder at different locations around the control panel.

12. A cart-borne ultrasound system having a control panel from which the system may be operated, and a hand-held probe connected to the system which transmits or receives ultrasound energy from a patient, comprising:

a plurality of probe holders located at different positions around the control panel, each probe holder having an extended position for use of the probe holder and a stowed position in which the probe holder cannot be used.

13. The cart-borne ultrasound system of claim 12, wherein the probe holder is pivoted from its stowed position to its extended position.

14. The cart-borne ultrasound system of claim 12, wherein the probe holder slides from its stowed position to its extended position.

15. The cart-borne ultrasound system of claim 12, wherein the stowed positions are beneath the control panel.

* * * * *